(12) United States Patent
Wilson

(10) Patent No.: US 9,290,522 B2
(45) Date of Patent: Mar. 22, 2016

(54) FUNCTIONALISED MATERIALS, PROCESS FOR THE PRODUCTION AND USES THEREOF

(75) Inventor: John Robert Howe Wilson, Abingdon (GB)

(73) Assignee: PHOSPHONICS LTD, Abingdon, Oxon (GB)

( * ) Notice: Subject to any disclaimer, the term of this patent is extended or adjusted under 35 U.S.C. 154(b) by 0 days.

(21) Appl. No.: 13/979,505

(22) PCT Filed: Jan. 12, 2012

(86) PCT No.: PCT/EP2012/000098
§ 371 (c)(1),
(2), (4) Date: Oct. 23, 2014

(87) PCT Pub. No.: WO2012/095307
PCT Pub. Date: Jul. 19, 2012

(65) Prior Publication Data
US 2015/0105575 A1    Apr. 16, 2015

(30) Foreign Application Priority Data

Jan. 13, 2011  (GB) .................... 1100531.1

(51) Int. Cl.
| C07F 7/08 | (2006.01) |
| C08G 77/28 | (2006.01) |
| C08G 77/50 | (2006.01) |

(52) U.S. Cl.
CPC .............. *C07F 7/0856* (2013.01); *C08G 77/28* (2013.01); *C08G 77/50* (2013.01)

(58) Field of Classification Search
CPC ........ C07F 7/0856; C08G 77/50; C08G 77/28
See application file for complete search history.

(56) References Cited

U.S. PATENT DOCUMENTS

| 2,727,920 A | 12/1955 | Johnson et al. |
| 4,552,700 A | 11/1985 | Panster et al. |
| 5,354,831 A * | 10/1994 | Panster ............ B01J 31/10 528/30 |
| 5,756,545 A | 5/1998 | O'Brien et al. |
| 5,919,566 A | 7/1999 | Lansink-Rotgerink et al. |
| 5,922,900 A | 7/1999 | Wieland et al. |
| 6,531,629 B1 | 3/2003 | Eiermann et al. |
| 2009/0098082 A1* | 4/2009 | Wilson .................. C08G 77/50 424/78.08 |

FOREIGN PATENT DOCUMENTS

| CN | 1662579 A | 8/2005 |
| CN | 101023120 A | 8/2007 |
| CN | 101405325 A | 4/2009 |
| CN | 101868467 A | 10/2010 |
| DE | 4223539 C1 | 11/1993 |
| EP | 0765897 A2 | 4/1997 |
| EP | 1142640 A1 | 10/2001 |
| EP | 1786850 A1 | 5/2007 |
| WO | 2006013060 A1 | 2/2006 |

OTHER PUBLICATIONS

Diaz, I., Mohino, F., Blasco, T., Sastre, E., Perez-Pariente, J., Influence of the alkyl chain length of HSO3-R-MCM-41 on the esterification of glycerol with fatty, Microporous and Mesoporous Materials vol. 80, 2005, pp. 33-42.

Alekseev, S.A., Zaitsev, V.N., Fraissard, J. Synthesis and structure of grafted layer of silicas modified with alkanesulfonic acid. Russian Chemical Bulletin, Feb. 2003, vol. 52, Issue 2, pp. 364-369.

Alekseev, S.A., Zaitsev, V.N., Fraissard, J., Organosilicas with Covalently Bonded Groups under Thermochemical Treatment. Chem. Mater., 2006, 18 (7), pp. 1981-1987.

European Search Report and Written Opinion as it relates to International Application No. PCT/EP2012/000098 dated Jul. 16, 2013.

International Preliminary Report on Patentability and Written Opinion for International Application No. PCT/EP2012/000098. Dated Jul. 16, 2013. 6 pages.

* cited by examiner

*Primary Examiner* — Sudhakar Katakam

(74) *Attorney, Agent, or Firm* — Lathrop & Gage LLP; Brian C. Trinque; Benjamin D. Heuberger

(57) ABSTRACT

The invention relates both to processes for the production of functionalised materials containing alkyl sulfonic acids groups and their use as heterogeneous catalysts. The invention also relates to precursors of these new products and new organopolysiloxane sulfonic acids.

13 Claims, No Drawings

FUNCTIONALISED MATERIALS, PROCESS FOR THE PRODUCTION AND USES THEREOF

The invention relates both to a process for the production of functionalised materials containing alkyl sulfonic acid groups and their use as heterogeneous catalysts. The invention also relates to precursors of these new products and new organopolysiloxane sulfonic acids.

There is a growing requirement in the chemical industry for effective heterogeneous catalysts to replace homogeneous reagents and catalysts. This requirement is as a consequence of stricter environmental regulations, the need to avoid and reduce solid and liquid waste levels along with the drive to lower energy consumption. For example there is a need for effective heterogeneous acid catalysts that can replace sulfuric acid, hydrogen fluoride or phosphoric acid. Additional advantages include ease of work up as heterogeneous acid catalysts can be readily separated whilst homogeneous catalysts require extensive work up and separation and so produces additional waste. Further advantages include being able to reuse the heterogeneous catalyst, selectivity for the production of the desired product and high thermal and physical stability. Further potential advantages include tuning the acid strength so as to avoid side reactions. For example sulfuric acid often produces coloured products that have to be purified. The additional purification process invariably produces additional waste and invariably requires additional energy consumption.

Sulfonic acid containing polymers and materials are used for a variety of purposes including purification of aqueous streams through the removal of metal ions and also as solid acid catalysts. The most common material is based on a sulfonated polystyrene polymer. The chemical and physical properties of such polystyrene based systems are described in the Bio-Rad Life Science Research Products catalogue 1998/99, pages 56-64. However the physical and chemical properties of these polystyrene resins may possess disadvantages, for example poor chemical stability and thermal stability, believed to be due to the organic polymeric backbone. Additional problems for example swelling and shrinking in organic solvents as well as the production of highly coloured unwanted side products may also be encountered. The swelling may cause problems in space use efficiency of reactors and production yield. Generally, due to their poor thermal stability, these polystyrene resins cannot be used for any length of time above 80° C., thus limiting their general applicability.

Inorganic polymer systems such as silica, aluminium oxide and titanium oxide have also been disclosed as functionalised materials. Active functional groups or metals can be attached by a variety of means to these systems. However a number of problems may be encountered where the functional groups are only physically adsorbed for example low functional group loading, limitations in the range of solvents that can be used, and removal of the functional groups during use or on standing. This is believed to be due to the rather weak attachment between the functional group and the surface atoms on the support. Building the functional group into the framework may provide a more robust material and may also allow higher functional group loadings. However in this approach there is a significant lack of readily available starting materials as well as precursors for preparing such starting materials. In addition there are limited synthetic methodologies for the preparation of suitable starting materials from available precursors. A need exists to provide new synthetic methods as well as starting compounds in order to make such functionalised materials. In addition even if such substrates are available the chemical processes to make the desired solid materials are invariably multi step, complex and leading to low yields and likely low functional group loadings of product that cannot be purified.

Acid catalysts based on propyl sulfonic acid attached to silica have been reported in U.S. Pat. No. 4,552,700. The process as described to make these catalysts involves multiple chemical steps and intermediate isolation and as a consequence has significant cost and manufacturing issues. In reality these processes are limited to the preparation of the propyl sulfonic acid material. Existing chemistry to make the ethyl sulfonic acid attached to silica is even more limited. One possible approach would involve a multi step process to first make and isolate the intermediates $(R^1O)_3SiCH_2CH_2SH$ or $[(R^1O)_3SiCH_2CH_2]_2S_n$, followed by oxidation and grafting. The intermediates can be formed in low yield through reaction with the unstable and not readily available $(R^1O)_3SiCH_2CH_2Cl$. This is not a realistic industrial process. The synthesis of these intermediates was reported in 1968 by Gornowicz et al. *J. Org. Chem* 1968. 33, 2918-2924 and again involved a multi step chemical process with a purification step. Vinyl trimethoxysilane was added into a heated mixture of thioacetic acid and azobisisobutyronitrile to give a mixture of $(CH_3O)_3SiCH_2CH_2SC(=O)CH_3$ and $(CH_3O)_3SiCH(CH_3)S-C(=O)CH_3$. Distillation was then required in order to separate $(CH_3O)_3SiCH_2CH_2S-C(=O)CH_3$ from its by-product $(CH_3O)_3SiCH(CH_3)S-C(=O)CH_3$. A second step involved the treatment of these compounds with sodium methoxide to form the desired compound $(CH_3O)_3SiCH_2CH_2SH$. Another process to prepare $(R^1O)_3SiCH_2CH_2SH$ was described in GB791609. In this case, vinyl triethoxysilane was refluxed with hydrogen sulfide under ultra-violet light. The drawback of this methodology is that the reaction takes place very slowly in the absence of ultra-violet light and this methodology does not lend itself to large scale manufacture.

Oxidation of $(R^1O)_3SiCH_2CH_2SH$ or $[(R^1O)_3SiCH_2CH_2]_2S_n$ to the desired intermediate $(R^1O)_3SiCH_2CH_2SO_3H$ is problematic and no successful reports of this chemical transformation could be found in the literature. Likewise no reference could be found for the silanol $(HO)_3SiCH_2CH_2SO_3H$.

It is an object of the present invention to provide processes for the production of ethyl sulfonic acids covalently attached to an inorganic material such as silica. A further object of the present invention is their use as heterogeneous catalysts.

In the first aspect the invention provides a process for the production of a compound of Formula I:

$$[(O_{3/2})SiCH_2CH_2SO_3X]_a\,[Si(O_{4/2})]_b\,[VSi(O_{3/2})]_c \qquad (I)$$

wherein:

X is selected from H, or M where M is a base or transition metal ion;

V is a monovalent group which is optionally substituted and selected from a $C_{1-22}$-alkyl group, $C_{2-22}$-alkenyl group, a $C_{2-22}$-alkynyl group, $C_{1-22}$-alkylaryl group, an aryl group, a $C_{2-20}$-alkyl sulfide $C_{1-22}$ alkyl group, $C_{2-20}$-alkylene sulfide alkyl group, a $C_{2-20}$-alkyl sulfide aryl group, a $C_{2-20}$-alkylene sulfide aryl group;

the free valences of the silicate oxygen atoms are saturated by one or more of:

a silicon atom of other groups of Formula I, hydrogen, a linear or branched $C_{1-22}$-alkyl group, an end group $R_3SiO_{1/2}$, a cross-linking bridge member or by a chain $R_qSi(OR^1)_gO_{k/2}$ or $Al(OR^1)_{3-h}O_{h/2}$ or $RAl(OR^1)_{2-r}O_{r/2}$, wherein R and $R^1$ are independently selected from a linear or branched $C_{1-12}$ alkyl group, an aryl group and a $C_{1-22}$ alkylaryl group, k is an integer from 1 to 3, q is an integer from 1 to 2 and g is an integer from 0 to 2 such that g+k+q=4, h is an integer from 1 to 3; and r is an integer from 1 to 2; and, when present, the ratio of the mole sum of the end group, cross linker and/or polymer chain to a+b+c is from 0 to 999:1 a, b and c are integers such that the ratio of a:b is from 0.00001 to 100000, a and b are always greater than 0 and when c is greater than 0 the ratio of c to a+b is from 0.00001 to 100000;

the process comprising contacting in any order or simultaneously:

a) a compound of Formula II or precursor components of the compound of Formula II,

$(R^3O)_3SiCH_2CH_2SC(=O)R^2$ (II)

where $R^3$ is hydrogen or a $C_{1-6}$ alkyl group and $R^2$ is a $C_{1-22}$ alkyl group, b) an inorganic support selected from silica, silica aluminate and alumina or with a compound selected from $Si(OR^1)_4$ and mixture of $Si(OR^1)_4$ and $Al(OR^1)_3$; and optionally one or more of $(R^3O)_3SiV$, $RSi(OR^3)_3$, $(R)_2Si(OR^3)_2$ and $(R)_3Si(OR^3)$, $Al(OR^3)_3$ and $RAl(OR^3)_2$; and c) nitric acid or hydrogen peroxide;

to produce the compound of Formula I.

The reactants are contacting under such conditions of reaction time, temperature and pressure and relative quantities that they react to produce the compound of Formula I.

In a preferred embodiment the precursors of compound of Formula II include vinyl trimethoxy silane and thioacetic acid and these are reacted together and then contacted with silica and nitric acid to produce a compound of Formula I.

The invention further provides to a process for the production of compounds of Formula I:

$[(O_{3/2})SiCH_2CH_2SO_3X]_a [Si(O_{4/2})]_b [VSi(O_{3/2})]_c$ where X is H or M where M is a transition or base metal salt; V is a group which is optionally substituted and selected from a $C_{1-22}$-alkyl group, $C_{1-22}$-alkylaryl group, an aryl group, a $C_{2-20}$-alkyl sulfide $C_{1-22}$ alkyl group, $C_{2-20}$-alkylene sulfide alkyl group, a $C_{2-20}$-alkyl sulfide aryl group, a $C_{2-20}$-alkylene sulfide aryl group; the free valences of the silicate oxygen atoms are saturated by one or more of:

a silicon atom of other groups of Formula I, hydrogen, a linear or branched $C_{1-22}$-alkyl group, an end group $R_3M^1O_{1/2}$, a cross-linking bridge member or by a chain $R_qM^1(OR^1)_gO_{k/2}$ or $Al(OR^1)_{3-h}O_{h/2}$ or $RAl(OR^1)_{2-r}O_{r/2}$;

wherein $M^1$ is Si or Ti; R and $R^1$ are independently selected from a linear or branched $C_{1-22}$ alkyl group, an aryl group and a $C_{1-22}$-alkylaryl group;

k is an integer from 1 to 3, q is an integer from 1 to 2 and g is an integer from 0 to 2 such that g+k+q=4;

h is an integer from 1 to 3; and r is an integer from 1 to 2;

or an oxo metal bridging system where the metal is zirconium, boron, magnesium, iron, nickel or a lanthanide;

a, b and c are integers such that the ratio of a:b is from 0.00001 to 100000 and a and b are always present and when c is greater than 0 the ratio of c to a+b is from 0.00001 to 100000.

Where an end group and/or cross linker and/or polymer chain is used, it is preferred that the ratio of end group, cross linker or polymer chains to a+b+c is from 0 to 999:1 preferably 0.001 to 999:1 and especially 0.01 to 99:1.

The optionally substituted linear or branched group selected from $C_{1-22}$-alkyl, $C_{2-22}$-alkenyl, $C_{2-22}$-alkynyl group, an aryl and $C_{1-22}$-alkylaryl group, R and $R^1$ groups may independently be linear or branched and/or may be substituted with one or more substituents but preferably contain only hydrogen and carbon atoms. If substituents are present, they may be selected independently from nitro, chloro, fluoro, bromo, nitrile, hydroxyl, carboxylic acid, carboxylic esters, sulfides, sulfoxides, sulfones, $C_{1-6}$-alkoxy, a $C_{1-22}$-alkyl or aryl di substituted phosphine, amino, amino $C_{1-22}$-alkyl or amino di ($C_{1-22}$-alkyl) or $C_{1-22}$-alkyl phosphinic or phosphonic group.

Preferably, the optionally substituted linear or branched group selected from $C_{1-22}$-alkyl, $C_{2-22}$-alkenyl, $C_{2-22}$-alkynyl group, an aryl and $C_{1-22}$-alkylaryl group, R and $R^1$ are independently selected from linear or branched $C_{1-22}$ and desirably $C_{1-12}$-alkyl, $C_{2-22}$- and desirably $C_{2-12}$-alkenyl, aryl and a $C_{1-22}$-alkylaryl group and it is especially preferred that these groups are independently selected from a linear or branched $C_{1-8}$-alkyl, $C_{2-8}$-alkenyl, aryl and a $C_{1-8}$-alkylaryl group.

Suitable groups R and $R^1$ are independently a $C_{1-6}$-alkyl group for example methyl or ethyl, or a phenyl group. Preferably q is from 0 to 2, k is from 1 to 3 and g is 0 provided that g+k+q=4.

Examples of suitable alkyl groups include methyl, ethyl, isopropyl, n-propyl, n-butyl, tert-butyl, n-hexyl, 2-hexyl n-decyl, n-dodecyl, cyclohexyl, n-octyl, cyclooctyl, iso-octyl, hexadecyl, octadecyl, iso-octadecyl and docosyl. Examples of suitable alkenyl groups include ethenyl, isopropenyl, cyclohexenyl, octenyl, iso-octenyl, hexadecenyl, octadecenyl, iso-octadecenyl and docosenyl.

$C_{1-6}$-alkoxy refers to a straight or branched hydrocarbon chain having from one to six carbon atoms and attached to an oxygen atom. Examples include methoxy, ethoxy, propoxy, tert-butoxy and n-butoxy.

The term aryl refers to a five or six membered cyclic, 8-10 membered bicyclic or 10-13 membered tricyclic group with aromatic character and includes systems which contain one or more heteroatoms, for example, N, O or S. Examples of suitable aryl groups include phenyl, pyridinyl, and furanyl. Where the term "alkylaryl" is employed herein, the immediately preceding carbon atom range refers to the alkyl substituent only and does not include any aryl carbon atoms. Examples of suitable alkylaryl groups include benzyl, phenylethyl and pyridylmethyl.

Compounds where c is zero and the ratio of b:a is from 10,000 to 0.2 are preferred.

It is an object of the present invention to provide convenient industrial scale processes for the manufacture of compounds of Formula I in which product yields, costs, scale and/or purities are commercially satisfactory, and improved with respect to the prior art.

Without wishing to be bound by any theory, it is believed that the new processes proceed via the radical addition of thioalkanoic acid onto vinyl trialkoxysilane to provide compounds of Formula II $(R^1O)_3SiCH_2CH_2SC(=O)R^2$. Suitable groups for $R^2$ are a $C_{1-12}$-alkyl group or aryl group and preferred examples are methyl, ethyl or a phenyl group.

In one process, treatment of $(R^1O)_3SiCH_2CH_2SC(=O)R^2$, where both $R^1$ and $R^2$ are methyl, with nitric acid at temperatures from 20-130° C. for 0.1-48 hours followed by a grafting reaction with an inorganic material such as silica in a solvent such as but not limited to water or toluene at temperatures of between 60-130° C. for 1-48 hours gives compounds of Formula I where c is zero. The inclusion of compounds $(R^1O)_3SiV$ in the grafting reaction with the inorganic material provides a process to make compounds of Formula I where c is greater than zero. The advantages of this process include the de-protection and oxidation of compounds of Formula II to a desired intermediate in a one step reaction that requires no isolation and purification; the desired intermediate is in a form that can be readily grafted onto an inorganic material without any manipulation and in cheap solvents such as water; the component c can be readily added to the process; the manufacture is scalable and can be performed in one reactor without any isolation of the intermediates involved; and the process proceeds in high product yield.

The invention also provides novel precursor compounds for Formula I, the precursor being of Formula III [(R$^4$O)$_3$SiCH$_2$CH$_2$SO$_3$X] wherein X is selected from H or M where M is a base or transition metal ion; and R$^4$ is selected from hydrogen and a C$_{1-22}$ alkyl group.

The invention also provides a process of producing compounds of Formula III [(R$^4$O)$_3$SiCH$_2$CH$_2$SO$_3$X] comprising reacting a compound of Formula II with 20-100% nitric acid at temperatures from 60-130° C. for 0.1-12 hours.

In another variation of these processes, treatment of (R$^1$O)$_3$SiCH$_2$CH$_2$SC(=O)R$^2$ with a hydrogen peroxide solution containing sulfuric acid at temperatures from 0-110° C. for 1-48 hours followed by a grafting reaction with an inorganic material such as silica in a solvent such as but not limited to water at temperatures of between 60-130° C. for 1-48 hours gives compounds of Formula I where c is zero. The inclusion of compounds such as (R$^1$O)$_3$SiV in the reaction with the inorganic material provides a process to make compounds of Formula I where c is greater than zero.

In an alternative process, treatment of compounds of Formula II (R$^1$O)$_3$SiCH$_2$CH$_2$SC(=O)R$^2$ with an inorganic material such as silica in a solvent or combination of solvents at temperatures of between 60-130° C. for 1-48 hours, followed by filtration, washing and then reaction with nitric acid at temperatures from 20-130° C. for 0.1-48 hours gives compounds of Formula I where c is zero. The inclusion of compounds (R$^1$O)$_3$SiV in the reaction with the inorganic material provides a process to make compounds of Formula I where c is greater than zero.

The advantages of these processes include the de-protection and oxidation can be conducted in one step; the component c can be readily added to the process to lead to compounds of Formula I where c is greater than zero; the manufacture is scalable and can be performed without isolation of the intermediates involved; and the processes proceed in high product yield.

The concentration of the nitric acid in these processes can vary from 20 to 100% with 50-70% being preferred.

A wide range of solvents and combination of solvents can be used for the grafting reaction between the intermediate and the inorganic material and include aliphatic or aromatic hydrocarbons, alcohols, polar solvents like dimethyl formamide, and water. Preferred solvents are toluene and xylene. Preferred inorganic materials include silica, alumina and silica aluminates.

Compounds of Formula I can also be prepared using sol gel processes for the formation of the silica framework. The solution obtained from treatment of compounds of Formula II (R$^1$O)$_3$SiCH$_2$CH$_2$SC(=O)R$^2$ with nitric acid at temperatures from 20-110° C. for 1-48 hours is combined with tetraethyl orthosilicate in an aqueous alcohol solvent. The solution was allowed to stand at 20-80° C. for 1 to 30 days and the resultant solid was dried, washed and milled to the desired particle size of compounds of Formula I where c=0. Compounds of Formula I where c is greater than zero are formed through the addition of (R$^1$O)$_3$SiV along with the tetraethyl orthosilicate.

The invention also provides novel compounds of Formula I:

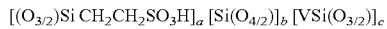

$[(O_{3/2})SiCH_2CH_2SO_3H]_a [Si(O_{4/2})]_b [VSi(O_{3/2})]_c$ wherein V is a group which is optionally substituted and selected from a C$_{1-22}$-alkyl group, C$_{1-22}$-alkylaryl group, an aryl group, a C$_{2-20}$-alkyl sulfide C$_{1-22}$ alkyl group, C$_{2-20}$-alkylene sulfide alkyl group, a C$_{2-20}$-alkyl sulfide aryl group, a C$_{2-20}$-alkylene sulfide aryl group; the free valences of the silicate oxygen atoms are saturated by one or more of:
  a silicon atom of other groups of Formula I, hydrogen, a linear or branched C$_{1-22}$-alkyl group, an end group R$_3$M$^1$O$_{1/2}$, a cross-linking bridge member or by a chain R$_q$M$^1$OR$^1$)$_g$O$_{k/2}$ or Al(OR$^1$)$_{3-h}$O$_{h/2}$ or RAl(OR$^1$)$_{2-r}$O$_{r/2}$;
wherein
  M$^1$ is Si or Ti; R and R$^1$ are independently selected from a linear or branched C$_{1-22}$ alkyl group, an aryl group and a C$_{1-22}$-alkylaryl group;
  k is an integer from 1 to 3, q is an integer from 1 to 2 and g is an integer from 0 to 2 such that g+k+q=4;
  h is an integer from 1 to 3; and
  r is an integer from 1 to 2;
  or an oxo metal bridging systems where the metal is zirconium, boron, magnesium, iron, nickel or a lanthanide;
  a, b and c are integers such that the ratio of a:b is from 0.00001 to 100000 and a and b are always present and when c is greater than 0 the ratio of c to a+b is from 0.00001 to 100000.

Where an end group and/or cross linker and/or polymer chain is used, it is preferred that the ratio of end group, cross linker or polymer chains to a+b+c is from 0 to 999:1 preferably 0.001 to 999:1 and especially 0.01 to 99:1.

Compounds of Formula I according to the invention are suitable for use as catalysts, especially as as heterogeneous acid catalysts. Compounds of Formula I are suitable for treating a feedstock of a reduction, elimination, alkylation, polymerisation, arylation, acylation, isomerisation, esterification, trans-esterification, elimination or rearrangement reaction. Suitably the feedstock is treated and the reaction carried out using a compound obtainable by a process according to the invention by contacting the compound with one or more reactants in the feedstock to catalyse the reaction.

In a preferred embodiment, the process comprises treating a feedstock comprising i) a carboxylic acid or compound comprising a reactable carboxylate moiety; and ii) and a compound comprising an alcohol group with a compound obtainable by a process according to the invention by contacting the compound and the feedstock to esterify the carboxylic acid or compound comprising a reactable carboxylate moiety. Preferably the carboxylic acid comprises a C$_{1-22}$ carboxylic acid, preferably a C$_{6-22}$ carboxylic acid. Examples of suitable carboxylic acids and reactable carboxylate moieties include maleic acid, acetic anhydride, dodecanoic acid, octanoic acid, oleic acid Suitably, the alcohol containing-compound comprises a polyalkylene glycol, preferably having from 1 to 100 alkylene oxide units, for example polyethylene glycol having an average molecular weight of 400. The alcohol may comprise a polyol, preferably glycerol, a glycol for example neopentyl glycol, trimethylolpropane, and pentaerythritol. The alcohol may be a C$_1$ to C$_{22}$, preferably C$_6$ to C$_{12}$ monoalcohol and may be linear, for example octan-1-ol, or branched, for example 2-ethyl hexanol.

Compounds of Formula I in which X is hydrogen have been found to be useful for catalysing a wide range of reactions, particularly reactions which are conventionally acid catalysed such as condensation reactions of aldehydes and ketones, ketalisation and acetalisation reactions, dehydration of olefins, a wide range of rearrangement and fragmentation reactions, isomerisations, esterifications and the trans-esterification of carboxylate esters. A particular advantage is that a material combining the advantages of a stable silica framework and the strong acid strength of the sulfonic acid group enables reactions to be conducted at high temperatures and pressures.

The invention will now be described in detail with reference to illustrative examples of the invention.

EXAMPLE 1

A mixture of vinyltrimethoxysilane (42.9 mL, 240 mmol) and di-tert-butyl peroxide (2 mL) was added dropwise over 20 min to a stirred solution of thioacetic acid (26.6 mL, 312 mmol) at reflux (86° C.). Reflux was maintained for a total of 3 h and the solution cooled and then added dropwise to a stirred solution of concentrated nitric acid (68%, 210 mL) at room temperature. After addition was complete, the mixture was heated at reflux for a further 90 min and then diluted to a volume of 510 mL with deionised water. Silica (171 g) was added and the mixture stirred at reflux for 6 h and then cooled. The filtered solid was washed with water (3×500 mL) and then methanol (3×500 mL) and dried to give a compound of Formula I where c=0.

EXAMPLE 2

A mixture of vinyltrimethoxysilane (42.9 mL, 240 mmol) and di-tert-butyl peroxide (2 mL) was added dropwise over 20 min to a stirred solution of thioacetic acid (26.6 mL, 312 mmol) at reflux (86° C.). Reflux was maintained for a total of 3 h. A Dean-Stark head was then added and excess thioacetic acid (7 mL) removed by distillation. The solution was cooled and then added dropwise to a stirred solution of concentrated nitric acid (68%, 210 mL) at room temperature. After addition was complete, the mixture was heated at reflux for a further 90 min and then diluted to a volume of 490 mL with deionised water. Silica (180 g) was added and the mixture stirred at reflux for 6 h and then cooled. The filtered solid was washed with water (3×500 mL) and then methanol (3×500 mL) and dried to give a compound of Formula I where c=0.

EXAMPLE 3

A mixture of vinyltrimethoxysilane (166.5 mL, 1.09 mol) and di-tert-butyl peroxide (5 mL) was added dropwise over 20 min to a stirred solution of thioacetic acid (100 mL, 1.42 mol) at reflux (86° C.). Reflux was maintained for a total of 3 h and the solution cooled and then added dropwise to a stirred solution of concentrated nitric acid (68%, 470 mL) at room temperature. After addition was complete, the mixture was heated at reflux for a further 90 min and then diluted to a volume of 2.34 L with deionised water. Butyltrimethoxysilane (9.72 g, 54.5 mmol) and silica (779 g) were added and the mixture stirred at reflux for 6 h and then cooled. The filtered solid was washed with water (3×2.3 L) and then methanol (2×2.3 L) and dried to give a compound of Formula I where V is butyl.

EXAMPLE 4

A mixture of vinyltrimethoxysilane (83.3 mL, 545 mmol) and di-tert-butyl peroxide (2 mL) was added dropwise over 20 min to a stirred solution of thioacetic acid (50.0 mL, 710 mmol) at reflux (86° C.). Reflux was maintained for a total of 6 h and the solution cooled and then added dropwise to a stirred solution of concentrated nitric acid (68%, 230 mL) at room temperature. After addition was complete, the mixture was heated at reflux for a further 90 min and then diluted to a volume of 500 mL with deionised water. A solution of tetraethyl orthosilicate (363 mL, 1.64 mol) in methanol (500 mL) was added and the mixture was heated at 50-60° C. for 14 days. The solid was milled, washed with water and then methanol and dried to give a compound of Formula I where c=0.

EXAMPLE 5

A mixture of vinyltrimethoxysilane (17.1 mL, 95 mmol) and thioacetic acid (10.6 mL, 125 mmol) were stirred at room temperature (18-28° C.) with UV irradiation for a total of 7 h. The solution was then added dropwise to a stirred solution of concentrated nitric acid (68%, 85 mL) at room temperature. After addition was complete, the mixture was heated at reflux for a further 90 min and then diluted to a volume of 200 mL with deionised water. Silica (65 g) was added and the mixture stirred at reflux for 6 h and then cooled. The filtered solid was washed with water (3×200 mL) and then methanol (3×200 mL) and dried to give a compound of Formula I where c=0.

EXAMPLE 6

Into a 75 L reactor was added thioacetic acid (6.93 kg, 91 mol) and toluene (10.70 L).

Agitation was applied and the solution was heated to 90° C. Vinyl trimethoxy silane (10.37 kg, 70 mol) and di tert-butyl peroxide (150 mL) was added slowly over 30 min. The solution was stirred under reflux for a further 4 hours at this temperature whilst adding di-tert-butyl peroxide every hour (400 mL in total) and then cooled. This solution was added into a stirred mixture of silica (50 kg) and toluene (120 L) in a 500 L reactor. The mixture was heated at reflux for 4 hours and the methanol produced in the reaction was removed. The mixture was cooled and filtered. The solid was washed with methanol and dried. The solid was then added to a stirred solution of nitric acid (69%, 150 L) at 114° C. for 4 hours to give a material of Formula I (56.5 kg) where c=0.

EXAMPLE 7

Vinyltrimethoxysilane (1.037 kg, 7 mol) and di-tert-butyl peroxide (150 mL) was added to a stirred solution of mercaptoacetic acid (0.693 kg, 9.1 mol) and toluene (1.7 L) at 90° C. The solution was stirred under reflux for 4 hours and then cooled to room temperature. This solution along with dodecyl trimethoxy silane (0.1 mol) was added into a stirred mixture of silica (5 kg) and toluene (12 L). The mixture was refluxed for 4 hours and during this phase the methanol produced in the reaction was removed. The mixture was cooled and filtered. The solid was washed with methanol and dried. The solid was then added to a stirred solution of nitric acid (69%) at 114 ° C. for 4 hours to give a material of Formula I (56.5 kg) where V was dodecyl.

EXAMPLE 8

A mixture of vinyltrimethoxysilane (166.5 mL, 1.09 mol) and di-tert-butyl peroxide (5 mL) was added dropwise over 20 min to a stirred solution of thioacetic acid (100 mL, 1.42 mol) at reflux (86° C.). Reflux was maintained for a total of 3 h and the solution cooled and then added dropwise to a stirred solution of concentrated nitric acid (68%, 470 mL) at room temperature. After addition was complete, the mixture was heated at reflux for a further 90 min and then diluted to a volume of 2.34 L with deionised water. 2-octylsulfidoethyl trimethoxysilane (54.5 mmol) and silica (779 g) were added and the mixture stirred at reflux for 6 h and then cooled. The filtered solid was washed with water (3×2.3 L) and then methanol (2×2.3 L) and dried to give a compound of Formula I where and V is 2-octylsulfideethyl.

EXAMPLE 9

A mixture of vinyltrimethoxysilane (166.5 mL, 1.09 mol) and di-tert-butyl peroxide (5 mL) was added dropwise over 20 min to a stirred solution of thioacetic acid (100 mL, 1.42 mol) at reflux (86° C.). Reflux was maintained for a total of 3 h and the solution cooled and then added dropwise to a stirred solution of concentrated nitric acid (68%, 470 mL) at room temperature. After addition was complete, the mixture was heated at reflux for a further 90 min and then diluted to a volume of 2.34 L with deionised water. 2-octadecylsulfido-ethyl trimethoxysilane (54.5 mmol) and silica (779 g) were added and the mixture stirred at reflux for 6 h and then cooled. The filtered solid was washed with water (3×2.3 L) and then methanol (2×2.3 L) and dried to give a compound of Formula I where and V is 2-octadecylsulfidoethyl.

EXAMPLE 10

A mixture of vinyltrimethoxysilane (166.5 mL, 1.09 mol) and di-tert-butyl peroxide (5 mL) was added dropwise over 20 min to a stirred solution of thioacetic acid (100 mL, 1.42 mol) at reflux (86° C.). Reflux was maintained for a total of 3 h and the solution cooled and added to sulfuric acid in water (10%, 450 mL). Hydrogen peroxide (30%, 376 mL, 4.36 mol) was added dropwise. After addition was complete, the mixture was heated at reflux for 30 min and then diluted to a volume of 2.34 L with deionised water. Silica (779 g) was added and the mixture stirred at reflux for 6 h and then cooled. The filtered solid was washed with water (3×2.3 L) and then methanol (2×2.3 L) and dried to give a compound of Formula I where c=0.

EXAMPLE 11

A mixture of maleic acid (23.2 g, 0.2 mol), 2-ethylhexanol (78.10 g, 0.6 mol), and the compound from Example 1 (0.38 g, 0.4 wt %) was heated on an oil bath at 130° C. with stirring under reduced pressure (~200 mbar). After 18 h, the mixture was cooled, filtered to recover catalyst, and analysed to show 97% diester present.

EXAMPLE 12

A mixture of maleic acid (23.2 g, 0.2 mol), 2-ethylhexanol (78.10 g, 0.6 mol), and the compound from Example 3 (0.38 g, 0.4 wt %) was heated on an oil bath at 120° C. with stirring under reduced pressure (~200 mbar). After 18 h, the mixture was cooled, filtered to recover catalyst, and analysed to 97% diester present.

EXAMPLE 13

A mixture of oleic acid (42.0 g, 148 mmol), glycerol (8.0 g, 87 mmol) and compound from Example 8 (0.5 g, 1 wt %) was heated with stirring to 150° C. under a gentle nitrogen flow (~0.1 L/min). After 24 h, the mixture was cooled and the catalyst filtered off. The pale yellow oil was analysed by standard titration techniques and found to have a hydroxy value of <0.1.

EXAMPLE 14

A mixture of oleic acid (42.0 g, 148 mmol), glycerol (8.0 g, 87 mmol) and compound from Example 1 (0.5 g, 1 wt %) was heated with stirring to 150° C. under a gentle nitrogen flow (~0.1 L/min). After 24 h, the mixture was cooled and the catalyst filtered off. The pale yellow oil was analysed by standard titration techniques and found to have a hydroxy value of <0.1.

EXAMPLE 15

A mixture of dodecanoic acid (19.4 g, 96.9 mmol), poly (ethylene glycol) (average molecular weight 400, 22.4 g, 56.0 mmol), and compound from Example 1 (0.4 g, 1 wt %) was heated on an oil bath at 120° C. with stirring under a gentle nitrogen flow. After 21 h, the mixture was cooled, filtered to recover catalyst, and analysed to show complete conversion of the dodecanoic acid.

EXAMPLE 16

A mixture of dodecanoic acid (19.4 g, 96.9 mmol), poly (ethylene glycol) (average molecular weight 400, 22.4 g, 56.0 mmol), and compound from Example 6 (0.4 g, 1 wt %) was heated on an oil bath at 120° C. with stirring under a gentle nitrogen flow. After 21 h, the mixture was cooled, filtered to recover catalyst, and analysed to show complete conversion of the dodecanoic acid.

EXAMPLE 17

A mixture of octanoic acid (46.2 g, 320 mmol, 3.2 eq), trimethylolpropane (13.8 g, 103 mmol, 1 eq), and the compound from Example 1 (0.06 g, 0.1 wt %) was heated on an oil bath at 140° C. with stirring. After 24 h, the mixture was cooled, filtered to recover catalyst, and analysed to show full conversion of the alcohol to diester (17%) and triester (83%).

EXAMPLE 18

A mixture of 1-octanol (40 mL, 252 mmol), acetic anhydride (26 mL, 278 mmol) and compound from Example 1 (0.6 g, 1 wt %) was stirred at 16° C. for 2 h. The solution was filtered and excess acetic anhydride removed by distillation to give 1-octyl acetate as the only product.

EXAMPLE 19

Into a 75 L reactor was added thioacetic acid (6.93 kg, 91 mol) and toluene (10.70 L). Agitation was applied and the solution was heated to 90° C. Vinyl trimethoxy silane (10.37 kg, 70 mol) and di tert-butyl peroxide (150 mL) was added slowly over 30 min. The solution was stirred under reflux for a further 4 hours at this temperature whilst adding di-tert-butyl peroxide every hour (400 mL in total) and then cooled. This solution was added into a stirred mixture of silica (50 kg) and nitric acid (120 L) in a 500 L reactor. The mixture was heated at reflux for between 2 to 6 hours and the methanol produced in the reaction was removed. The mixture was cooled and filtered. The solid was washed with water and methanol and dried to give a material of Formula I (56.5 kg) where c=0.

The stability of the catalyst was tested by refluxing in methanol for 200 hours. The catalyst had a similar final acid loading after this test as to the loading before the test, indicating excellent stability.

EXAMPLE 20

The procedure of Example 19 was repeated but with the mixture being refluxed for between 12 and 24 hours. The stability of the catalyst was tested and shown to have retained the acid loading and showed excellent stability. Beyond 200 hours, the catalyst maintained its acid loading for a longer period than the catalyst of Example 19 indicating a higher level of stability.

The invention claimed is:

1. A process for the production of a compound of Formula I:

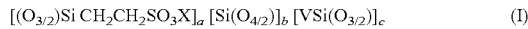

$$[(O_{3/2})Si\,CH_2CH_2SO_3X]_a\,[Si(O_{4/2})]_b\,[VSi(O_{3/2})]_c \qquad (I)$$

wherein:
X is selected from H, or M where M is a base or transition metal ion;
V is a monovalent group which is optionally substituted and selected from a $C_{1-22}$-alkyl group, $C_{2-22}$-alkenyl group, a $C_{2-22}$-alkynyl group, $C_{1-22}$-alkylaryl group, an aryl group, a $C_{2-20}$-alkyl sulfide $C_{1-22}$ alkyl group, $C_{2-20}$-alkylene sulfide alkyl group, a $C_{2-20}$-alkyl sulfide aryl group, a $C_{2-20}$-alkylene sulfide aryl group;
the free valences of the silicate oxygen atoms are saturated by one or more of:
a silicon atom of other groups of Formula I, hydrogen, a linear or branched $C_{1-22}$-alkyl group, an end group $R_3SiO_{1/2}$, a cross-linking bridge member or by a chain $R_q Si(OR^1)_g O_{k/2}$ or $Al(OR^1)_{3-h} O_{h/2}$ or $RAl(OR^1)_{2-r} O_{r/2}$, wherein R and $R^1$ are independently selected from a linear or branched $C_{1-12}$ alkyl group, an aryl group and a $C_{1-22}$-alkylaryl group, k is an integer from 1 to 3, q is an integer from 1 to 2 and g is an integer from 0 to 2 such that g +k +q =4, h is an integer from 1 to 3; and r is an integer from 1 to 2; and, when present, the ratio of the mole sum of the end group, cross linker and/or polymer chain to a+b+c is from 0 to 999:1 a, b and c are integers such that the ratio of a:b is from 0.00001 to 100000, a and b are always greater than 0 and when c is greater than 0 the ratio of c to a+b is from 0.00001 to 100000;
the process comprising contacting in any order or simultaneously:
a) a compound of Formula II or precursor components of the compound of Formula II,

$$(R^3O)_3SiCH_2CH_2SC(=O)R^2 \qquad (II)$$

b) where $R^3$ is hydrogen or a $C_{1-6}$ alkyl group and $R^2$ is a $C_{1-22}$ alkyl group, an inorganic support selected from silica, silica aluminate and alumina or with a compound selected from $Si(OR^1)_4$ and mixture of $Si(OR^1)_4$ and $Al(OR^1)_3$; and optionally one or more of $(R^3O)_3SiV$, $RSi(OR^3)_3$, $(R)_2Si(OR^3)_2$ and $(R)_3Si(OR^3)$, $Al(OR^3)_3$ and $RAl(OR^3)_2$; and
c) nitric acid or hydrogen peroxide; to produce the compound of Formula I.

2. A process according to claim 1 wherein the process comprises contacting a compound of Formula II: either with:
a) an inorganic support selected from silica, silica aluminate and alumina or with a compound selected from $Si(OR^1)_4$ and mixture of $Si(OR^1)_4$ and $Al(OR^1)_3$; and optionally one or more of $(R^3O)_3SiV$, $RSi(OR^3)_3$, $(R)_2Si(OR^3)_2$ and $(R)_3Si(OR^3)$, $Al(OR^3)_3$ and $RAl(OR^3)_2$ to produce a reaction product and contacting the reaction product with nitric acid or hydrogen peroxide to produce the compound of Formula I; or
b) with nitric acid to produce a reaction product and contacting the reaction product and optionally one or more of $(R^3O)_3SiV$, $RSi(OR^3)_3$, $(R)_2Si(OR^3)_2$ and $(R)_3Si(OR^3)$, $Al(OR^3)_3$ and $RAl(OR^3)_2$ with an inorganic support selected from silica, silica aluminate and alumina or with a compound selected from $Si(OR^1)_4$ and mixture of $Si(OR^1)_4$ and $Al(OR^1)_3$;
to produce a compound of Formula I.

3. A process according to claim 1 wherein the compound of Formula II is present as a solution of the compound of Formula II.

4. A process according to claim 1 wherein compound of Formula II is reacted with an inorganic support selected from silica, silica aluminate and alumina wherein the reaction is carried out at 20 to 150° C. for between 10 minutes to 48 hours to produce the reaction product.

5. A process according to claim 1 wherein the said process comprises reacting a solution of Formula II, where $R^3$ is hydrogen or a $C_{1-6}$ alkyl and $R^2$ is a $C_{1-6}$ alkyl, and optionally one or more of $(R^1O)_3SiV$, $RSi(OR^1)_3$, $(R)_2Si(OR^1)_2$ and $(R)_3Si(OR^1)$, $Al(OR^1)_3$ and $RAl(OR^1)_2$ with the inorganic support at 80 to 150° C. for between 10 minutes to 8 hours, and treating the resultant product with nitric acid at 20° C. to 130° C. for between 10 minutes to 8 hours.

6. A process according to claim 1 wherein the contacting step comprises sol gelling the compound of Formula II with a compound selected from $Si(OR^1)_4$ and a mixture of $Si(OR^1)_4$ and $Al(OR^1)_3$ and optionally one or more of $(R^1O)_3SiV$, $RSi(OR^1)_3$, $(R)_2Si(OR^1)_2$ and $(R)_3Si(OR^1)$, $Al(OR^1)_3$ and $RAl(OR^1)_2$ to produce a reaction product and contacting the reaction product with nitric acid or hydrogen peroxide to produce the compound of Formula I.

7. A process according to claim 1 wherein the reaction product is reacted with nitric acid at 0° C. to 150° C. for between 10 minutes to 12 hours to produce a compound of Formula I.

8. A process according to claim 1 comprising contacting a compound of Formula II with nitric acid to produce a reaction product and contacting the reaction product and optionally one or more of $(R^1O)_3SiV$, $RSi(OR^1)_3$, $(R)_2Si(OR^1)_2$ and $(R)_3Si(OR^1)$, $Al(OR^1)_3$ and $RAl(OR^1)_2$ with an inorganic support selected from silica, silica aluminate and alumina or with a compound selected from $Si(OR^1)_4$ and mixture of $Si(OR^1)_4$ and $Al(OR^1)_3$ to produce a compound of Formula I.

9. A process according to claim 8 wherein the compound of Formula II is contacted with nitric acid at a temperature from 20-130° C. for 10 minutes to 48 hours.

10. A process according to claim 8 wherein the reaction product is reacted with the inorganic support selected from silica, silica aluminate and alumina at 20 to 140° C. for between 10 minutes to 48 hours.

11. A process according to claim 10 wherein the reaction is carried out for between 10 minutes and 8 hours.

12. A process according to claim 8 wherein a compound of Formula II, wherein $R^1$ is hydrogen or a $C_{1-6}$ alkyl is treated with 50-70% nitric acid nitric acid at temperatures from 60-130° C. for 10 minutes to 12 hours.

13. A process according to claim 1 where the integer c in Formula I is zero, the free valences of the silicate oxygen atoms are saturated by one or more of a silicon atom of other groups of Formula I, hydrogen, a linear or branched $C_{1-6}$-alkyl group; $R^3$ in Formula II is hydrogen or a $C_{1-6}$ alkyl and $R^2$ is a $C_{1-6}$ alkyl.

* * * * *